United States Patent
Srivastava et al.

(10) Patent No.: US 7,390,792 B2
(45) Date of Patent: Jun. 24, 2008

(54) MICRORNA1 THERAPIES

(75) Inventors: Deepak Srivastava, Orinda, CA (US); Chulan Kwon, San Francisco, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 128 days.

(21) Appl. No.: 11/303,862

(22) Filed: Dec. 15, 2005

(65) Prior Publication Data

US 2007/0142313 A1   Jun. 21, 2007

(51) Int. Cl.
*A61K 31/70* (2006.01)
*C07H 21/04* (2006.01)
*C12N 15/00* (2006.01)

(52) U.S. Cl. .................... 514/44; 536/24.5; 435/455

(58) Field of Classification Search ............. None
See application file for complete search history.

(56) References Cited

U.S. PATENT DOCUMENTS

2005/0059005 A1 * 3/2005 Tuschl et al. .................. 435/6

OTHER PUBLICATIONS

Patel et al. Cancer Research 2005, vol. 65, pp. 8690-8697.*
Purow et al. Cancer Research 2005, vol. 65, pp. 2353-2363.*
Opalinska et al. Nature Reviews Drug Discovery, 2002, vol. 1, p. 503-514.*
Brennecke et al. Genes & Development 2005, vol. 19, pp. 2261-2264.*
Zhao et al. Nature 2005, vol. 436, pp. 214-220.*
Opalinska et al. Nature Reviews Drug Discovery, 2002, vol. 1, p. 503-514.*

* cited by examiner

*Primary Examiner*—Tracy Vivlemore
(74) *Attorney, Agent, or Firm*—Richard Aron Osman

(57) ABSTRACT

Delta protein expression in a cell is reduced by introducing miR-1 into the cell, and detecting a resultant reduction of Delta protein expression in the cell.

12 Claims, No Drawings

MICRORNA1 THERAPIES

FIELD OF THE INVENTION

The field of the invention is the use of microRNA1 to inhibit Delta protein expression.

BACKGROUND OF THE INVENTION

MicroRNAs (miRNAs) are 21-22 nucleotide non-coding RNAs that are sometimes expressed in a lineage-specific fashion and thus have the potential to control cell fate decisions (Ambros, 2001; Bartel, 2004; Johnston, 2003). There are over 300 known miRNAs and each is thought to target numerous mRNA transcripts for either degradation or, more often, translational inhibition. miRNAs typically bind to 3' untranslated regions (UTRs) of mRNAs through inexact sequence matching. The lack of precise sequence homology between miRNA and targets has made target prediction difficult, although it does appear that sequence matching of the 5' end of the miRNA and a permissive secondary structure of target mRNA are important features (Lewis, 2003; Zhao, 2005). Despite recent advances in target prediction, only a handful of miRNA targets have been validated thus far resulting in limited knowledge of biological roles for most miRNAs.

miRNAs may play a role in regulation of stem cell fates (Hatfield, 2005; Forstemann, 2005; Cheng, 2005), but direct experimental evidence and a mechanistic understanding of miRNA regulation of cell lineages have been lacking. In *Drosophila*, the dorsal vessel, a primitive heart, is composed of distinct cell types, each arising from progenitor cells that follow stereotypic lineage decisions, providing a tractable system in which to study the possible involvement of miRNAs in cell fate decisions. We previously demonstrated that miR-1-1 and miR-1-2 are redundant muscle-specific mammalian miRNAs that play a role in cardiogenesis (Zhao, 2005). Mouse miR-1-1 and miR-1-2 were regulated by serum response factor (SRF), a central transcriptional regulator of muscle differentiation, and excess miR-1 in vivo resulted in premature withdrawal of cardiomyocytes from the cell cycle. We have found that miR-1 targets the Notch ligand Delta, and that when introduced into cells, inhibits Delta protein expression.

SUMMARY OF THE INVENTION

The invention provides methods of reducing Delta protein expression in a cell, comprising the steps of: introducing into the cell miR-1; and detecting a resultant reduction of Delta protein expression in the cell.

The cell may be in vitro or in situ; in specific embodiments, the cell is a mammalian cell, such as of a cancer wherein the Delta protein is predetermined to be upregulated. In particular embodiments, the Delta protein is Delta-like-4 (Dll4).

DETAILED DESCRIPTION OF SPECIFIC EMBODIMENTS OF THE INVENTION

The invention provides methods and compositions for using miR-1 to inhibit Delta protein expression. The subject methods generally comprise the steps of: introducing an effective amount of miR-1 into a cell expressing the Delta protein; and detecting a resultant reduction of Delta protein expression in the cell. The subject compositions include miR-1 medicaments formulated for delivery according to the disclosed methods.

Preferred Delta proteins are mammalian "Delta-like ligands of Notch", particularly Delta-like-1 (Dll1), Delta-like-3 (Dll3), and Delta-like-4 (Dll4). In particular embodiments the Delta protein is predetermined to be upregulated or overexpressed in the target cell; particularly wherein Dll1, Dll3, or Dll4 is predetermined to be upregulated in a mammalian target cell; particularly wherein the cell is a pathogenic cell, such as a cancer cell; particularly of a cancer wherein the Delta protein is upregulated, such as renal cell carcinomas, gliomas and cervical cancers (see e.g. Patel, 2005; Puro, 2005). In particular embodiments, the cell is selected from a myoblast, an endothelial cell, and a lymphoblast. The target cell may be in vitro or in situ. Routine methods such as Western blot, ELISA, etc. can be used to determine whether Delta is upregulated in the target cell relative to control cells (e.g. renal carcinoma cells versus matched normal kidney cells).

In the introducing step, genomic DNA that expresses the miR-1 can be introduced into the cell. For example a plasmid can be constructed with genomic sequence containing pre-miR-1 gene sequences plus flanking sequences, and transfected into the cell using standard protocols (see e.g. Zhao, 2005). Alternatively miR-1 can be directly introduced into the cell. The sequence of miR-1 is well-known across numerous species, including human (e.g. Zhao, 2005), and can be readily synthesized. Methods known for synthesizing dsRNA and introducing them into cells are applicable to making and delivering the subject microRNAs (see e.g. WO/017164 to Tuschl et al; and U.S. Pat. No. 6,506,559 to Fire et al). Custom-made RNAs are also commercially available (e.g. Ambion Inc., Austin, Tex.).

For cells in vitro, introduction can be accomplished by direct injection into cells. Delivery can often be enhanced by using hydrophobic or cationic carriers such as Lipofectamine™ (Invitrogen, Carlsbad, Calif.). Peptides such as penetratin, transportan, Tat peptide, nuclear localization signal (NLS), and others, can also be attached to the miR-1 to promote cellular uptake. Alternatively, the cells can be permeabilized with a permeabilization agent such as lysolecithin, and then contacted with the miR-1. Viral transduction can be used to deliver miR-1 to cells in vitro (e.g. lentiviral transduction, SV40 vector (Rund, 1998) etc.). For cells in situ, cationic lipids (Hassani et al, 2005) and polymers such as polyethylenimine (see e.g. Urban-Klein, 2005) may be used to facilitate RNA delivery. Compositions consisting essentially of the miR-1 (in a carrier solution) can also be directly injected locally or systemically into the host of the target cell.

The miR-1 is optionally chemically modified to enhance a desired property of the molecule. For example, modifications can be made to increase the serum stability and half-life when administered in vivo. Examples of serum stability-enhancing chemical modifications include phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation (see e.g. US Patent Publication No. 20050032733 to McSwiggen et al). A broad spectrum of chemical modifications can be made to RNA, without negatively impacting the inhibitory properties. A variety of 2' modifications are known in the art (see e.g. U.S. Pat. No. 5,859,221 to Cook et al.; U.S. Pat. No. 6,673,611 to Thompson et al.).

Resultant reduced Delta expression can be measured directly, such as determined by Western blot or ELISA; indirectly, such as through Notch binding or signalling; or inferentially through a metric pre-correlated with Delta protein expression, such as a downstream phenotypic change indicative of reduced Delta expression, e.g. a reduced proliferation or differentiation, etc. In particular embodiments, the resultant reduction is quantitatively detected, and where inferentially detected, the metric is quantitatively pre-correlated with Delta protein expression.

EXAMPLES

I. We found several conserved putative miR-1 binding sites in the 3'-UTR of the gene encoding Drosophila Delta. We introduced one of the putative miR-1 binding sites from the Delta 3'-UTR into the 3'-UTR of luciferase in the presence or absence of miR-1 in Drosophila S2 cells. Introduction of the miR-1 binding site resulted in dose-dependent and specific down-regulation of luciferase activity in the presence of dmiR-1, indicating that Delta is a miR1 target. We next sought to confirm this by demonstrating an effect by miR-1 on Delta protein levels in vivo. We employed an in vivo assay involving the well-described role of Delta-Notch signaling in the developing wing disc, where disruption of Delta results in thickening of fly wing veins (Huppert, 1997; Muskavitch, 1994). Delta protein is normally detectable and expressed in two perpendicular stripes in the wing pouch. We overexpressed miR-1 along one of the two stripes using a dpp-Gal4 driver and assayed the effects on Delta protein expression. Delta protein was markedly reduced exclusively in the domain of miR-1 expression, providing in vivo confirmation of Delta as a target of miR-1. miR-1-induced loss of Delta in this specific sub-domain of the wing resulted in thickening of wing veins, recapitulating the loss-of-Delta phenotype. The shortened leg phenotype upon miR-1 overexpression provided further evidence of miR-1's effects on the Notch pathway, as this too was similar to the phenotype of flies lacking Delta (de Celis, 1998). Together, the in vivo experiments provided compelling evidence that miR-1 can be used to regulate Delta protein levels.

II. We identified a putative miR-1 binding site in the 3'-UTR of the mammalian homolog of Delta, Delta-like-4 (Dll4). C2C 12 mouse myoblasts were transfected with miR-1 using previously described methods (Zhao, 2005). Briefly, the genomic sequence containing pre-miR-1 gene sequences plus about 50 bp flanking each side is inserted into pcDNA3. Plasmid transfection is performed in 12-well plates using FuGENE 6 (Roche). Western blot was performed using standard methods with specific antibodies. miR-1 significantly decreased Dll4 expression in C2C12 cells compared to controls.

III. Dll4 is a selective inhibitor of VEGF-A biological activities and downregulates VEGF receptor-2 (Williams, 2005). Dll4-expressing HUVECs display reduced proliferative responses selectively to VEGF-A. Using previously described methods (Williams, 2005) human umbilical vein endothelial cells (HUVECs) are retrovirally transduced with Dll4 and proliferation in response to VEGF-A is measured with and without mi-R1 treatment. Briefly, the cDNA of human full-length Dll4 (Gen Bank AF253468) is cloned from placental cDNA and cloned into pGEM-T easy vector (Promega). Dll4 is cut from the vector, ligated into a retroviral plasmid and transfected into the Phoenix viral packaging cell line (Orbigen, San Diego, Calif.) and cultured with HUVECs. miR-1 is microinjected into HUVECs and proliferation is measured by $^3$H-thymidine deoxyribose uptake. Reconstitution of the proliferative phenotype demonstrates miR-1 inhibition of Delta expression.

IV. Dll4 expression in T cells enhances activation and proliferation (Rutz, 2005). To demonstrate its anti-proliferative effect on leukemia cells, the following T-cell leukemia cell lines are microinjected with miR-1: MOLT-4, MT-2, MT-4, SLB-1, C5/MJ, HUT-102, MT-1, and ED-40515 (Mori, 2005). The cells are maintained in culture with RPMI 1650 supplemented with 10% FBS (HyClone), 50-U/ml penicillin, and 50 µg/ml streptomycin at 37° C. in 5% $CO_2$. The cells are incubated in microtiter plates and growth inhibition assays are performed using a WST-8 cell counting kit (Wako Chemicals, Osaka, Japan). Western blot analysis demonstrates dose-dependent reduced Dll4 expression in miR-1 treated cells relative to controls.

V. Lethally irradiated mice reconstituted with bone marrow cells transduced to overexpress Dll4 develop a lethal phenotype that is characterized by a progression of a T-cell lymphoproliferative disease to transplantable monoclonal T-cell leukemia/lymphoma scattered to multiple organs (Yan, 2001). This mouse model is used to demonstrate the anti-proliferative effect of intravenously administered miR-1 on leukemia cells. Concurrent with bone marrow transplantation, mice receive daily miR-1 injections or saline control. After four weeks and 19 weeks, the lymph nodes, spleen, peripheral blood and bone marrow in miR-1 treated versus control-treated mice are analyzed. In control mice, overexpression of Dll4 blocks the development of B cells and alters the development of T cells as various stages (Yan, 2001). B cell and T cell development in miR-1 treated mice more closely resembles that of normal mice (that do not receive the irradiation/bone marrow transplant treatment). Histopathology in miR-1 treated mice reveals liver and lymph nodes that resemble normal mice while saline control mice have enlarged lymph nodes and livers with lymphoblastic infiltration.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

REFERENCES

Ambros, 2001. Cell 107:823-826.
Bartel, 2004. Cell 116:281-297.
Cheng et al, 2005. Neuron 46:363-367.
de Celis et al, 1998. Development 125:4617-4626.
Forstemann et al, 2005. PloS. Biol. 3, e236
Hassani et al, 2005. J Gene Med. February 2005;7(2):198-207.
Hatfield et al, 2005. Nature 435:974-978.
Huppert et al, 1997. Development 124:3283-3291.
Johnston et al, 2003. Nature 426:845-849.
Lewis et al, 2003. Cell 115:787-798.
Mori et al, 2004. J. Virol. 78:4582-4590
Muskavitch et al, 1994. Dev. Biol. 166:415-430.
Patel et al. 2005, Cancer Res 65: 8690-8697.
Puro et al, 2005. Cancer Res 65:2353-2363.
Rund et al, 1998. Hum Gene Ther. 9:649-57.
Rutz et al, 2005. Eur. J. Immunol. 35:2443-2451.
Urban-Klein et al, 2005. Gene Ther. 12:461-6.
Williams et al, 2005. Blood. October 11; [Epub ahead of print; PMID: 16219802]
Yan et al, 2001. Blood. 98:3793-9.
Zhao et al, 2005. Nature 436:214-220.

What is claimed is:
1. A method of reducing Notch ligand Delta protein expression in a mammalian cell in vitro, comprising the steps of:

introducing into the cell miR-1; and detecting a resultant reduction of the Delta protein expression in the cell, wherein the Delta protein is Delta-like-4 (Dll4).

2. The method of claim 1 wherein the Delta protein is predetermined to be overexpressed or upregulated in the cell.

3. The method of claim 1 wherein the cell is selected from a myoblast, an endothelial cell, and a lymphoblast.

4. The method of claim 1 wherein the cell is of a cancer wherein the Delta protein is predetermined to be upregulated.

5. The method of claim 1 wherein the cell is of a cancer wherein the Delta protein is predetermined to be upregulated, the cancer selected from the group consisting a renal cell carcinoma, glioma and cervical cancer.

6. The method of claim 1 wherein the resultant reduction of Delta protein in the cell is detected directly by Western blot or ELISA.

7. The method of claim 1 wherein the resultant reduction of Delta protein in the cell is detected indirectly by detecting a change in Delta-Notch binding or signaling.

8. The method of claim 1 wherein the resultant reduction of Delta protein in the cell is detected by detecting a change in cell proliferation or differentiation pre-correlated with Delta protein expression.

9. The method of claim 1 wherein the resultant reduction is quantitatively detected.

10. The method of claim 1 wherein:
    the cell is selected from a myoblast, an endothelial cell, and a lymphoblast; and
    the Delta protein is predetermined to be overexpressed or upregulated in the cell.

11. The method of claim 1 wherein the cell is of a cancer wherein the Delta protein is predetermined to be upregulated, and the resultant reduction of Delta protein in the cell is detected by detecting a change in cell proliferation or differentiation pre-correlated with Delta protein expression.

12. The method of claim 1 wherein the cell is of a cancer wherein the Delta protein is predetermined to be upregulated, and the resultant reduction is quantitatively detected.

\* \* \* \* \*